United States Patent
Keim et al.

(10) Patent No.: US 10,518,042 B2
(45) Date of Patent: Dec. 31, 2019

(54) NEEDLE CAP REMOVER AND DRUG DELIVERY DEVICE

(71) Applicant: Sanofi-Aventis Deutschland GmbH, Frankfurt am Main (DE)

(72) Inventors: Moritz Keim, Mainz (DE); Winfried Huthmacher, Frankfurt (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 439 days.

(21) Appl. No.: 15/037,938

(22) PCT Filed: Nov. 25, 2014

(86) PCT No.: PCT/EP2014/075558
§ 371 (c)(1),
(2) Date: May 19, 2016

(87) PCT Pub. No.: WO2015/078869
PCT Pub. Date: Jun. 4, 2015

(65) Prior Publication Data
US 2016/0354551 A1 Dec. 8, 2016

(30) Foreign Application Priority Data
Nov. 28, 2013 (EP) ..................... 13194895

(51) Int. Cl.
*A61M 5/32* (2006.01)

(52) U.S. Cl.
CPC ........ *A61M 5/3204* (2013.01); *A61M 5/3257* (2013.01); *A61M 5/326* (2013.01); *A61M 2005/3267* (2013.01)

(58) Field of Classification Search
CPC ........ A61M 5/3204; A61M 2005/3247; A61M 5/3202
See application file for complete search history.

(56) References Cited

U.S. PATENT DOCUMENTS 4,636,201 A    1/1987  Ambrose et al.
4,979,945 A *  12/1990  Wade .................. A61M 5/3213
                                              206/365

(Continued)

FOREIGN PATENT DOCUMENTS

WO    WO2012/073032    7/2012

OTHER PUBLICATIONS

International Search Report and Written Opinion in International Application No. PCT/EP2014/075558, dated Mar. 3, 2015, 15 pages.

(Continued)

*Primary Examiner* — Brandy S Lee
(74) *Attorney, Agent, or Firm* — Fish & Richardson P.C.

(57) ABSTRACT

The invention refers to a needle cap remover (7) for a needle cap (5.1) of a drug delivery device (2). The needle cap remover (7) comprises a body (8) having a material which differs from the material of the needle cap (5.1) or of a rigid needle shield (5) encasing the needle cap (5.1) in at least one parameter, wherein a body portion (8.1), which covers the needle cap (5.1) or the rigid needle shield (5) encasing the needle cap (5.1), is adapted to capture the needle cap (5.1) or the rigid needle shield (5) encasing the needle cap (5.1) by a positive and/or non-positive connections before or during removing of the needle cap (5.1) and is adapted to shrunk when a pulling force is applied.

16 Claims, 2 Drawing Sheets
Specification includes a Sequence Listing.

(56) References Cited

U.S. PATENT DOCUMENTS

| | | | |
|---|---|---|---|
| 6,485,460 B2* | 11/2002 | Eakins | A61M 5/3134 |
| | | | 604/111 |
| 2007/0239114 A1* | 10/2007 | Edwards | A61M 5/19 |
| | | | 604/131 |
| 2007/0265568 A1 | 11/2007 | Tsals et al. | |
| 2010/0069846 A1 | 3/2010 | Stamp | |

OTHER PUBLICATIONS

International Preliminary Report on Patentability in International Application No. PCT/EP2014/075558, dated May 31, 2016, 10 pages.

Rote Liste, "50. Hypophysen-, Hypothalamushormone, andere regulatorische Peptide u. ihre Hemmstoffe," Chapter 50, ed. 2008, 20 pages.

* cited by examiner

```
                        SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39), insulin analogue or derivative

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

NEEDLE CAP REMOVER AND DRUG DELIVERY DEVICE

CROSS-REFERENCE TO RELATED APPLICATIONS

This application is a U.S. national stage application under 35 USC § 371 of International Application No. PCT/EP2014/075558, filed on Nov. 25, 2014, which claims priority to European Patent Application No. 13194895.2, filed on Nov. 28, 2013, the entire contents of which are incorporated herein by reference.

SEQUENCE LISTING

The document includes a sequence listing in electronic format submitted to the United States Patent and Trademark Office via the electronic filing system. The ASCII text file, which is incorporated-by-reference herein, is titled "37488-0451US1.txt," was created on Aug. 11, 2016, and has a size of 823 bytes.

TECHNICAL FIELD

The invention relates to a needle cap remover for removing a needle cap from a needle of a drug delivery device, and to such a drug delivery device.

BACKGROUND OF THE INVENTION

Many drug delivery devices of the prior art, such as auto-injectors, syringes, have been developed for self-administration of the drug.

To protect the needle of the drug delivery device from damage or to protect people from needle-prick injuries before using of the device, the needle of the drug delivery device is covered by a protective needle cap of a flexible material which can be encased by a rigid, in particular a plastic needle shield, the so-called rigid needle shield (shortly named RNS).

In order to prepare the drug delivery device for delivering a dose the protective needle cap has to be removed from the needle. This may be done by gripping the protective needle cap and pulling it away from the needle. This will usually result in an exposed needle which is undesirable in terms of needle safety or for person with a needle phobia.

In order to solve that problem the needle of the drug delivery device could be covered by a needle shield or shroud in a manner to hide the needle when the protective needle cap is removed.

SUMMARY OF THE INVENTION

Certain aspect of the present invention relate to a needle cap remover which is together with the needle cap removable in a reliable way. Certain aspect of the present invention relate to a drug delivery device with an improved needle cap remover.

Preferred embodiments of the invention are given in the dependent claims.

According to the invention, a needle cap remover for a needle cap of a drug delivery device is provided which comprises a body having a material which differs from the material of the needle cap in at least one parameter, wherein a body portion, which covers the needle cap at least in part, is adapted to capture the needle cap or a rigid needle shield encasing the needle cap by a positive and/or non-positive connection during or before removing of the needle cap or the encasing rigid needle shield but not during assembling, in particular when the needle cap remover is pulled for removing the needle cap or the encasing rigid needle shield.

In this manner, that the positive and/or non-positive connection between the needle cap remover and the needle cap or the rigid needle shield encasing the needle cap is not formed during assembling but before or during removing the needle cap or the encasing rigid needle shield, the needle cap is only stressed by axial forces. In other words: Only axial forces impact on the protective needle cap during assembly. Thus, it is ensured that damages are prevented and the needle will not be contaminated during assembly and will be sterile.

Preferably, the body of the needle cap remover and the needle cap or the rigid needle shield encasing the needle cap differs in at least one of the following parameters, e.g. in material, in resistance, in stiffness, in size and/or in heat resistance.

In the context of this specification, the term "back" or "proximal" end of a component or of a device refers to the end closest to the user's hand or furthest away from the delivery or injection site and the term "front" or "distal" end of a component or device refers to the end furthest from the user's hand or closest to the delivery or injection site.

In a possible embodiment, the body portion is formed as a shrinking hose arranged as an outer wall onto the needle cap or onto the rigid needle shield encasing the needle cap and heat shrunk onto the needle cap or onto the encasing rigid needle shield. This concept allows an engaging of the needle cap remover to the needle cap or to the encasing rigid needle shield by an adhesive connection. In particular, the needle cap remover and the needle cap or the encasing rigid needle shield differ at least in the material and/or in the heat resistance. In a possible embodiment the needle cap is formed as an inner needle cap of a flexible material. The needle cap may be covered by the rigid needle shield (shortly named RNS) which is made of a rigid polypropylene cap wherein the needle cap remover is made of a thermoplastic material, e.g. fluoropolymer, polyolefine, PVC material or similar materials.

In an exemplary embodiment, the shrinking hose is formed as a sleeve of high impact resistance, in particular of a thermoplastic material, wherein the coupling between the shrinking hose and the needle cap or the encasing rigid needle shield is induced by a heating during assembly. Due to the low wall thickness of the shrinking hose, the shrinking hose is arranged to the needle cap or to the encasing rigid needle shield and both together can be assembled to the drug delivery device before a needle shield of the drug delivery device will be assembled. After the needle cap remover and the needle cap or the encasing rigid needle shield are arranged to each other they are heated wherein the shrinking hose shrinks so that the needle cap remover and the needle cap or the encasing rigid needle shield are adhesively joined together such that, in use, if the needle cap remover is moved away from the drug delivery device, it takes the needle cap or the rigid needle shield encasing the inner needle cap with it and removes it from the drug delivery device too and thus from the needle.

Furthermore, the body comprises an opened and a closed end, wherein the closed end of the body and thus of the shrinking hose is formed as a dome from which a sleeve wall extends. At least the sleeve wall is made of a shrinkable material, e.g. a thermoplastic material. The outer surface of the dome comprises a gripping portion which is gripped by a user of the drug delivery device when the needle cap should be removed from the device. The gripping portion may have profiled structures, e.g. grooves, rips.

In an alternative embodiment, the body portion is formed as a fabric tube or textile arranged onto the needle cap or onto the rigid needle shield encasing the needle cap during assembling and mechanically shrunk onto the needle cap or the encasing rigid needle shield during removing. This concept allows an engaging of the needle cap remover to the needle cap or the encasing rigid needle shield by a positive and/or non-positive connection, e.g. a form-fitting and/or friction connection. In particular, the needle cap remover and the needle cap or the encasing rigid needle shield differs at least in the material and/or the resistance too, wherein the needle cap is made of a flexible material, e.g. rubber, and may be encased by the rigid needle shield which is made of a rigid polypropylene cap. The needle cap remover is made of a fabric or textile tube of rubber or silicon or similar materials, e.g. rubber-weave hose.

In a further embodiment, the fabric tube is formed as an open-ended, tubular sleeve made of textile, fabric, rubber or silicon. The fabric tube is cold applied and therefore quicker, easier and safer to assembly than the heat shrink conception. It allows a seal without adhesive and thus it is simple and fast to assemble. Preferably, the fabric tube together with the needle cap or the rigid needle shield encasing the needle cap can be assembled to the drug delivery device before the needle shield of the drug delivery device is assembled. If the user pulls off the closed end of a completely assembled drug delivery device, on which closed end for example a gripping label is arranged, the fabric tube contracts or shrinks in such a manner that the fabric tube and the needle cap are mechanically joint by a positive and/or non-positive connection, e.g. a form-fitting connection or friction connection, after assembling and during removing. In the case that the needle cap is connected to and encased by a rigid needle shield the needle cap remover is arranged onto the rigid needle shield. If the user pulls off the closed end of the needle cap remover, the fabric tube contracts or shrinks in such a manner that the fabric tube and the rigid needle shield are mechanically joint so that the rigid needle shield together with the needle cap is pulled away from the drug delivery device.

According to another feature of the invention, the fabric tube comprises as an inner element filling materials and/or inner threads. The filling material and/or the inner threads are preferably embedded in a wall of the body portion of the fabric tube. The fabric tube has further an opened end and a closed end wherein the close end is formed as a dome on which a safety element, e.g. a safety label, may be attached. Depending on the kind of drug delivery device, the safety element is arranged to the closed end in such a manner that it extends through an opening in a distal or front end of the needle shield of the drug delivery device.

In yet a further alternative embodiment, the body portion is formed as a hollow or flat and bend sheet metal part arranged onto the needle cap or onto the rigid needle shield encasing the needle cap and having protrusions directed inwards to engage the needle cap or the rigid needle shield. In a possible embodiment the protrusions are formed as hooks. Moreover, the sheet metal part comprises a plurality of rows of inwardly directed protrusions which dig into the outer surface of the needle cap or of the encasing rigid needle shield and form a positive and/or non-positive connection during removing of the needle cap or of the encasing rigid needle shield. Thus, the sheet metal part removes the needle cap or the rigid needle shield encasing the needle cap too by further movement. The plurality of inwardly directed protrusions provides a mechanical and thus simple and safe inter-engagement of the respective surfaces of the needle cap remover and the needle cap or the rigid needle shield encasing the needle cap to securely couple both parts and allow a common movement. The hooks may take a number of different forms. Preferably, the hooks are slightly angled and inwardly protrude into the direction of the movement of the needle cap remover. By pulling the needle cap remover into the opposite direction to the removal movement and thus push the body onto the drug delivery device, namely the needle cap or the rigid needle shield encasing the needle cap, the hooks slide over outer surface of the needle cap or of the encasing rigid needle shield. In use, when the needle cap remover is removed from the drug delivery device into the removal direction the hooks dig into the outer surface of the needle cap or the encasing rigid needle shield and are securely fixed during removing.

The invention also refers to a drug delivery device comprising a needle cap remover as it is above described. The described needle cap remover serves a safe and easy assembling to the drug delivery device wherein only axial force appears on the needle cap or the rigid needle shield encasing the needle cap during assembling so that needle damages are prevented and thus the needle will not be contaminated during assembly.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
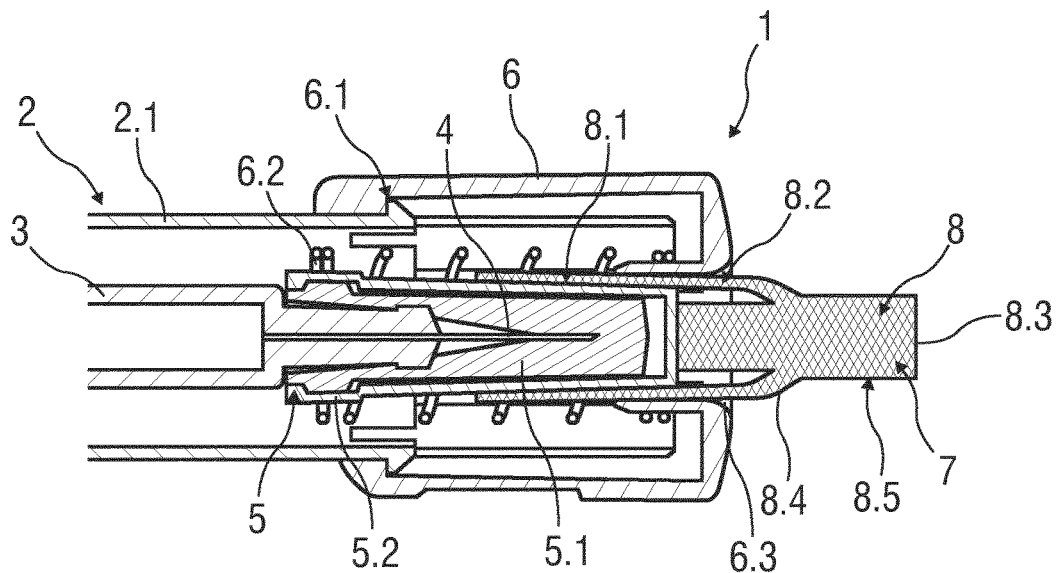
FIG. 1 shows a partial longitudinal section of a first embodiment of a drug delivery device with an improved needle cap remover.

FIG. 1 shows one embodiment of the present invention in a partial longitudinal section of a needle safety device 1 for a drug delivery device 2.

The drug delivery device 2 is a pre-filled syringe 3 having a needle 4. The needle 4 may be fixed to the distal end of the syringe 3 or removable therefrom, as a matter of design choice. The syringe 3 is held in a housing 2.1 of the drug delivery device 2. Alternatively, the drug delivery device could be an auto-injector with a container, an injection pen or a syringe to be filled or another medicament container or any other application with comparable functional principle. The housing 2.1 may be designed as a one part or multiple part housing capable of receiving and containing the container, in the embodiment the syringe 3.

The needle safety device 1 comprises a needle cap 5.1, a rigid needle shield 5 and a needle cap remover 7 which are adapted to be connected to each other by friction connection and/or positive locking connection and/or form-fitting connection.

As it can be seen, the drug delivery device 2 comprises further a needle shield 6. The needle shield 6 is being mounted on the housing 2.1 of the drug delivery device 2 in a movable manner by a snap-fit connection 6.1. A spring 6.2 biases at one end of the needle shield 6 and at the other end the housing 2.1.

The needle cap 5.1 is being mounted on the needle 4 in a separable manner. The needle cap 5.1 is designed as a resilient cap made of a flexible material which covers the needle 4 before use to protect it against damages during transport or travel and to keep it sterile during the assembly process. The needle cap 5.1 is encased by the rigid, in particular plastic, needle shield 5, the so called rigid needle shield (shortly named RNS). The needle cap 5.1 is of a typical form and is made of a rubber or a soft rubber or rubber like core for easier and safer handling. The rubber needle cap 5.1 and the rigid needle shield 5 are coupled by a latching element 5.2, e.g. a groove, which forms with corresponding outer profiled surface of the rubber needle cap 5.1 a positive and/or non-positive locking connection.

In an alternative, not shown embodiment, the needle safety device 1 comprises only the needle cap 5.1 without the rigid needle shield so that the needle cap remover 7 is directly arranged onto the needle cap 5.1. The function and the arrangement of the needle cap remover 7 directly onto the needle cap 5.1 or onto the rigid needle shield 5 encasing the needle cap 5.1 are identical and do not differ from each other. Thus, the following description regarding a needle cap remover arranged onto a rigid needle shield encasing a needle cap also applies to a needle cap remover directly arranged onto the needle cap without an encasing.

According to a first embodiment, the needle cap remover 7 comprises a body 8 having a material which differs from the material of the needle cap 5.1 and/or the rigid needle shield 5 in at least one parameter. In particular, the needle cap 5.1 is made of a rubber and the rigid needle shield 5 is made of rigid polypropylene cap with the inner rubber needle cap 5.1 and the needle cap remover 7 is made of a thermoplastic material, e.g. fluoropolymer, polyolefine, PVC material or similar materials.

The needle cap remover 7 is inserted through an opening 6.3 of the needle shield 6 and arranged onto the needle shield 5. In an alternative embodiment (not shown), the needle 4 is only covered by the rubber needle cap 5.1 so that the needle cap remover 7 is arranged onto the rubber needle cap 5.1 directly.

The following description refers to a drug delivery device with a rubber needle cap covered by a rigid needle shield. This description applies also for a drug delivery device only with a rubber needle cap without a rigid needle shield, wherein the needle cap remover described below is directly arranged onto the rubber needle cap.

A body portion 8.1 partly covers the rigid needle shield 5. The body portion 8.1 is adapted to capture the rigid needle shield 5 in the overlapping area by a positive and/or non-positive connection before removing of the rigid needle shield 5 but not during assembling.

To provide such a secured connection after assembling but before or during removing of the rigid needle shield 5, the body portion 8.1 is formed as a shrinking hose 8.2 arranged as an outer wall of the rigid needle shield 5 and heat shrunk onto the rigid needle shield 5 after assembling. Thus, only axial forces impact on the protective rigid needle shield 5 and thus on the needle cap 5.1 during assembly.

The shrinking hose 8.2 is formed as a sleeve of high impact resistance and with a low wall thickness. Furthermore, the shrinking hose 8.2 is made of a thermoplastic material, wherein the coupling between the shrinking hose 8.2 and the respective rigid needle shield 5 is induced by a heating during assembly. Due to the low wall thickness of the shrinking hose 8.2, the shrinking hose 8.2 together with the rigid needle shield 5 can be assembled to the drug delivery device 2 before the needle shield 6 will be assembled.

During heating of the assembled shrinking hose 8.2 and the rigid needle shield 5, the shrinking hose 8.2 shrinks so that the shrinking hose 8.2 and thus the needle cap remover 7 and the rigid needle shield 5 are adhesively joined together. In use, if the needle cap remover 7 is moved away from the drug delivery device 2, the rigid needle shield 5 will be moved in the same direction and thus it will be removed from the drug delivery device 2 together with the needle cap 5.1 too and thus from the needle 4.

To support the gripping of the needle cap remover 7, the body 8 comprises a closed end 8.3. The closed end 8.3 is formed as a dome from which a sleeve wall 8.4 extends. At least the sleeve wall 8.4 is made of a shrinkable material, e.g. a thermoplastic material, which is shrunk when a pulling force is applied at the closed end 8.3.

The outer surface of the dome comprises a gripping portion 8.5 which can be gripped by a user of the drug delivery device 2 when the rigid needle shield 5 should be removed from the device. The gripping portion 8.5 may be formed as profiled structures, e.g. grooves, rips.

Figure 2:
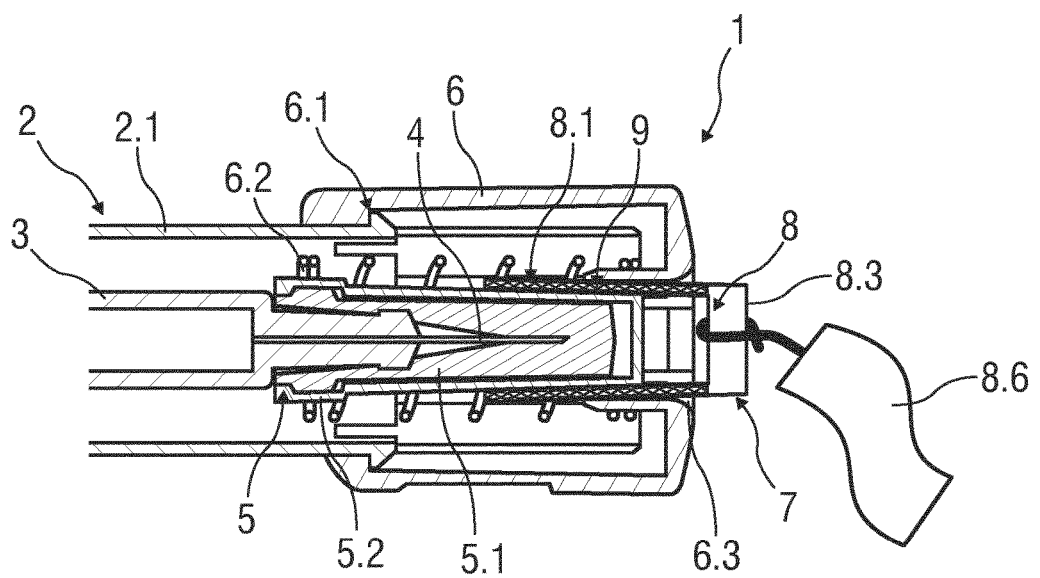
FIG. 2 shows a partial longitudinal section of a second embodiment of a drug delivery device with an alternative improved needle cap remover.

FIG. 2 shows an alternative embodiment of the invention which differs in the body 8 and the body portion 8.1. The body portion 8.1 is formed as a fabric tube 9 which extends from the closed end 8.3 of the body 8. The fabric tube 9 is designed to fit over the rigid needle shield 5 and is formed as an open-ended, tubular sleeve. The fabric tube 9 is arranged as an outer wall onto the rigid needle shield 5, wherein the fabric tube 9 is mechanically shrunk onto the rigid needle shield 5 by a positive and/or non-positive connection, e.g. a form-fitting and/or friction connection, when a pulling force is applied.

The needle cap remover 7 and the rigid needle shield 5 differs at least in the material, in the adhesion properties and/or the resistance, wherein the rigid needle shield 5 is made of a rigid polypropylene material and the needle cap remover 7 is made of a fabric or textile tube of a textile or rubber or silicon or similar materials, e.g. rubber-weave hose.

Preferably, the fabric tube 9 can be assembled to the rigid needle shield 5 and together with the rigid needle shield 5 to the drug delivery device 2 before the needle shield 6 of the drug delivery device 2 will be assembled.

The needle cap remover 7 comprises the closed end 8.3 which is formed as a bridge at which a gripping element 8.6 may be attached. Depending on the kind of drug delivery device 2, the gripping element 8.6 is arranged to the closed end 8.3 in such a manner that it extends through the opening 6.3 of the needle shield 6. As it is shown in FIG. 2, the gripping element 8.6 may be designed as a gripping label.

After assembling of the whole drug delivery device 2 and in use, a user grasps the needle cap remover 7 at the gripping element 8.6 arranged at the closed end 8.3 of the needle cap remover 7 and pulls it off. Due to this pulling movement, the fabric tube 9 contracts or shrinks in such a manner that the fabric tube 9 and the rigid needle shield 5 are mechanically joint by positive and/or non-positive connection, e.g. a form-fitting connection or friction connection, during removing and thus after assembling.

Additionally, the fabric tube 9 comprises at least one inner element 10 which may support the adhesion properties of the mechanical connection. The inner element 10 may be designed as a filling material and/or inner threads. The filling material and/or the inner threads are preferably embedded in a wall of the body portion 8.1 of the fabric tube 9.

Figure 3:
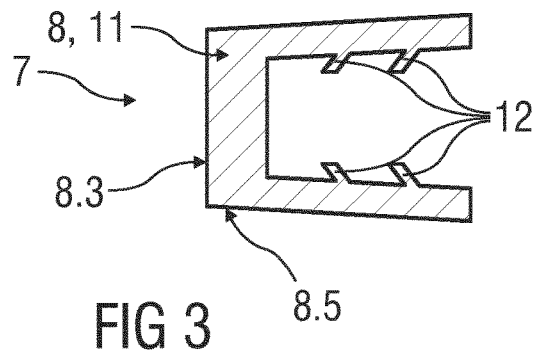
FIG. 3 shows a partial longitudinal section of a third embodiment of an improved needle cap remover.

FIG. 3 shows a partial longitudinal section of a third embodiment of a further improved needle cap remover 7. The body 8 is formed as a hollow sheet metal part 11 adapted to be arranged onto the rigid needle shield 5. The body 8 has a clamp shape or U-shape or the form of a sleeve or cylinder.

The body 8 is made of a thin sheet metal. Hence, the needle cap remover 7 and the rigid needle shield 5 differs at least in the material and/or the resistance, wherein the rigid needle shield 5 is made of a rigid polypropylene material and the needle cap remover 7 is made of a thin metal sheet profile.

Furthermore, the body 8 comprises protrusions 12 which extend from the inside wall into the inner hole. Preferably, the body 8 comprises a plurality of inwardly directed protrusions 12 which are formed as hooks. The hooks may take a number of different forms. Preferably, the hooks are slightly angled and inwardly protrude into the direction of the pull-off-movement of the needle cap remover 7.

Figure 4:
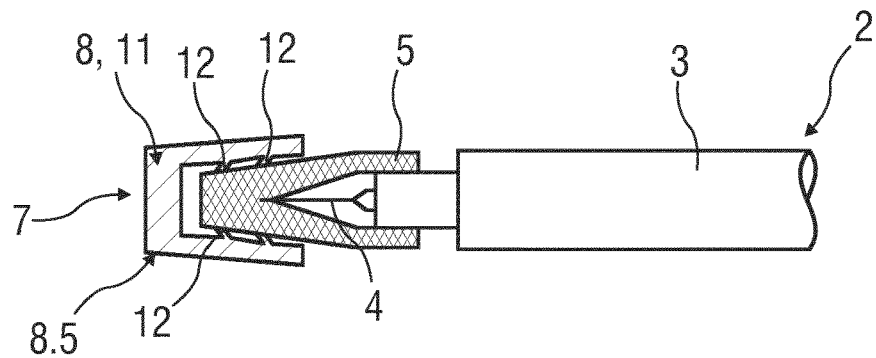
FIG. 4 shows the needle cap remover according to FIG. 3 assembled to a needle cap of a drug delivery device in a longitudinal section.

FIG. 4 shows the sheet metal part 11 assembled onto a rigid needle shield 5 for a needle 4 of a drug delivery device 2.

During assembling, the inwardly directed edges or protrusions 12 slide over the surface of the rigid needle shield 5 when the needle cap remover 7 is pushed upon the rigid needle shield 5. Pulling the needle cap remover 7 into the opposite direction and thus into the removing direction the protrusions 12 dig into the outer surface of the rigid needle shield 5 and thus form a positive and/or non-positive connection during removing of the rigid needle shield 5. Thus, the sheet metal part 11 removes the rigid needle shield 5 too by further movement.

Figure 5:
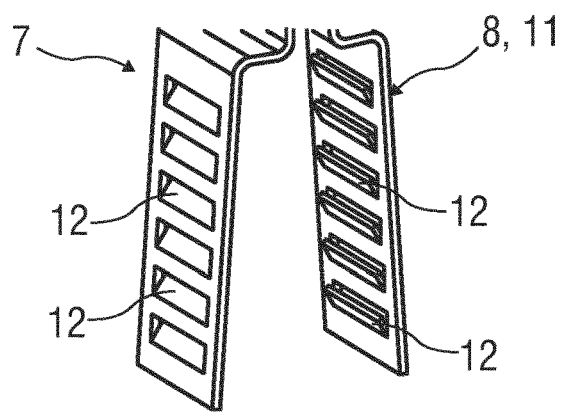
FIG. 5 shows a perspective view of an embodiment of a clamp-like needle cap remover.

FIG. 5 shows a perspective view of a possible embodiment of a needle cap remover 7. The needle cap remover 7 is designed as a clamp-like sheet metal part 11 with a plurality of inwardly directed protrusions 12 which are extended from each of the opposite inner surfaces in a row and in a respective distance to each other.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO:1).

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains ρ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically Acceptable Solvates are for Example Hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES

1 Needle safety device
2 Drug delivery device
3 Syringe
4 Needle
5 Rigid needle shield
5.1 Rubber needle cap
5.2 Latching element
6 Needle shield
6.1 Snap-fit connection
6.2 Spring
6.3 Opening
7 Needle cap remover
8 Body
8.1 Body portion
8.2 Shrinking hose
8.3 Closed end of the body
8.4 Sleeve wall
8.5 Gripping portion
8.6 Gripping element
9 Fabric tube
10 Inner element
11 Sheet metal part
12 Protrusion

The invention claimed is:

1. A needle cap remover for a needle cap of a drug delivery device, comprising:
a body having a material which differs from a material of the needle cap or a rigid needle shield encasing the needle cap in at least one parameter,
wherein a portion of the body, which covers the needle cap or the rigid needle shield encasing the needle cap, is adapted to capture the needle cap or the rigid needle shield encasing the needle cap before or during removing of the needle cap, wherein the portion of the body is formed as a shrinking hose adapted to be arranged onto the needle cap or onto the rigid needle shield encasing the needle cap and heat shrunk onto the needle cap or onto the rigid needle shield encasing the needle cap.

2. The needle cap remover according to claim 1, wherein the shrinking hose is formed as a sleeve of high impact resistance.

3. The needle cap remover according to claim 1, wherein a closed end of the body is formed as a dome from which a sleeve wall extends.

4. The needle cap remover according to claim 1, wherein the portion of the body is formed as a fabric tube that is adapted to be arranged onto the needle cap or onto the rigid needle shield encasing the needle cap and mechanically shrunk onto the needle cap or onto the rigid needle shield encasing the needle cap.

5. The needle cap remover according to claim 4, wherein the fabric tube is formed as an open-ended, tubular sleeve made of one or more of the following: fabric, textile, rubber and silicon.

6. The needle cap remover according to claim 4, wherein the fabric tube comprises an inner element comprising filling materials and/or inner threads.

7. The needle cap remover according to claim 6, wherein a gripping element is attached to a closed end of the body.

8. The needle cap remover according to claim 1, wherein the portion of the body is formed as a hollow sheet metal part adapted to be arranged onto the needle cap or onto the rigid needle shield encasing the needle cap and having protrusions directed inwards to engage the needle cap or the rigid needle shield encasing the needle cap.

9. The needle cap remover according to claim 8, wherein the sheet metal part comprises a plurality of inwardly directed protrusions which dig into the outer surface of the needle cap or of the rigid needle shield encasing the needle cap during removing of the needle cap.

10. The needle cap remover according to claim 1, wherein the shrinking hose is formed as a sleeve of thermoplastic material.

11. A drug delivery device comprising:
a housing; and
a needle cap remover comprising:
 a body having a material which differs from the material of the needle cap or a rigid needle shield encasing the needle cap in at least one parameter,
 wherein a portion of the body, which covers the needle cap or the rigid needle shield encasing the needle cap, is adapted to capture the needle cap or the rigid needle shield encasing the needle cap before or during removing of the needle cap, wherein the portion of the body is formed as a shrinking hose adapted to be arranged onto the needle cap or onto the rigid needle shield encasing the needle cap and heat shrunk onto the needle cap or onto the rigid needle shield encasing the needle cap.

12. The drug delivery device of claim 11, further comprising a pharmaceutically active compound disposed in the housing.

13. A drug delivery device comprising:
a housing comprising a syringe comprising a needle;
a needle safety device mounted on the housing, the needle safety device comprising a needle cap covering at least a distal tip of the needle; and
a needle cap remover configured to remove the needle cap to uncover the needle, the needle cap remover comprising:
 a body having a material which differs from the material of the needle cap,
 wherein a portion of the body, which covers the needle cap, is adapted to capture the needle cap before or during removing of the needle cap,
 wherein the portion of the body is formed as a shrinking hose adapted to be arranged onto the needle cap encasing the needle cap and heat shrunk onto the needle cap.

14. The drug delivery device of claim 13, wherein the needle safety device further comprises a needle shield connected to the needle cap remover by at least one of a friction connection, a positive locking connection or a form-fitting connection.

15. The drug delivery device of claim 13, wherein the body comprises a closed end formed as a dome, the closed end attached to a distal end of the portion of the body, wherein the portion of the body comprises a sleeve wall that extends from the closed end made of a shrinkable material configured to shrink in response to a distal pulling force on the closed end to remove the needle cap.

16. The drug delivery device of claim 15, wherein the body comprises a gripping portion disposed on an outer surface of the closed end, wherein the gripping portion is formed as profiled structures comprising at least one of grooves or rips.

* * * * *